United States Patent [19]

Hatanaka et al.

[11] Patent Number: 4,617,268
[45] Date of Patent: Oct. 14, 1986

[54] PROCESS FOR THE PREPARATION OF ADENOSINE-5'-TRIPHOSPHATE BY FERMENTATION

[75] Inventors: Masayoshi Hatanaka; Daizo Takeuchi, both of Iwaki, Japan

[73] Assignee: Kureha Kagaku Kogyo Kabushiki Kaisha, Tokyo, Japan

[21] Appl. No.: 551,498

[22] Filed: Nov. 14, 1983

Related U.S. Application Data

[63] Continuation of Ser. No. 226,913, Jan. 21, 1981, abandoned.

[51] Int. Cl.[4] .......................... C12P 19/32; C12N 1/32
[52] U.S. Cl. ........................................ 435/92; 435/247
[58] Field of Search .................................. 435/92, 247

[56] References Cited

U.S. PATENT DOCUMENTS

| | | | |
|---|---|---|---|
| 3,444,040 | 5/1969 | Nara et al. | 435/92 |
| 3,616,224 | 10/1971 | Kamakura et al. | 435/247 |
| 3,755,082 | 8/1973 | Terui et al. | 435/247 |
| 3,762,999 | 10/1973 | Nakayama | 435/92 |
| 3,764,476 | 10/1973 | Abe et al. | 435/247 |
| 3,767,533 | 10/1973 | Sugisaki et al. | 435/247 |
| 4,106,988 | 8/1978 | Ohsugi et al. | 435/247 |

OTHER PUBLICATIONS

Netrusov et al, FEBS Letters, vol. 76, No. 1, pp. 56–58, Apr. 1977.

Primary Examiner—Alvin E. Tanenholtz

[57] ABSTRACT

Disclosed in this invention is a process for the preparation of adenosine-5'-triphosphate by means of fermentation, using an adenosine-5-triphosphate-producing bacterium which assimilates methanol.

10 Claims, No Drawings

PROCESS FOR THE PREPARATION OF ADENOSINE-5'-TRIPHOSPHATE BY FERMENTATION

This application is a continuation of U.S. application Ser. No. 226,913, filed Jan. 21, 1981 now abandoned.

BACKGROUND OF THE INVENTION

This invention relates to a process for the preparation of adenosine-5'-triphosphate by means of fermentation, and more particularly it relates to a process for preparing adenosine-5'-triphosphate according to a fermentation method by utilizing the microorganisms having methanol assimilability.

Growing interest is shown recently on availability of adenosine-5'-triphosphate (hereinafter referred to as ATP) for medicines, biochemical reagents, etc., as this substance plays an important role for the metabolism of energy as a high-energy phosphate compound in the living organism. Studies are being made for use of an enzyme pyruvate kinase, which is capable of regenerating adenosine-5'-diphosphate into ATP, in the ATP regeneration system for allowing efficient utilization of ATP in a bioreactor using ATP. Thus, uncostly supply of ATP is required for the production of the biochemical substances and coenzymes such as flavin adenine dinucleotide, nicotinamide adenine dinucelotide, etc.

There are known several methods for the production of ATP such as direct isolation from the animal muscle, organic chemical synthesis, enzymatic phosphatization of 5'-adenylic acid and fermentation. Regarding the last-mentioned fermentation method, there have been proposed some different techniques including a method in which a bacterium belonging to *Brevibacterium ammoniagenes* is cultivated in a medium containing adenine or a derivative thereof to thereby produce and accumulate ATP (Japanese Patent Publication No. 17634/1966), a method in which a microorganism having ATP producibility is cultivated in a medium containing a surfactant and ATP is collected from the cultures (Japanese Patent Publication No. 28996/1974), and a method in which a compound having a phenolic hydroxyl group is added in the medium at a point when the ATP yield in the medium has reached the maximum (Japanese Patent Laying-Open No. 6490/1978).

However, in any of these conventional methods adopting fermentation techniques, fermentation is effected by including adenine or a derivative thereof such as adenosine in the culture medium, that is, such adenine or a derivative thereof is used as substrate and it is phosphatized to thereby produce and accumulate ATP. Thus, the conventional methods use expensive adenine or its derivatives as starting material and hence can hardly be termed as industrially advantageous means.

As a result of further studies on means for producing ATP industrially at low cost by using the fermentation techniques, we found that ATP is accumulated in a high concentration in the culture medium when an ATP-producing bacterium having methanol assimilability is cultivated in a medium containing methanol or a chemical substance showing the same metabolic route as methanol as well as a specified amount of an inorganic phosphate as substrate instead of expensive adenine or its derivatives. This invention was reached on the basis of such finding.

The principal object of this invention, therefore, is to provide a process capable of producing ATP in an industrially advantageous way by means of fermentation.

Other objects of this invention will become apparent from the following detailed description of the invention.

DETAILED DESCRIPTION OF THE INVENTION

The salient feature of this invention resides in selecting a microorganism which is capable of assimilating methanol to produce ATP and cultivating such ATP-producing microbe in a medium containing as substrate methanol or a chemical substance showing the same metabolic route as methanol as well as an inorganic phosphate in an amount of 4–35 g/l as calculated in terms of phosphoric acid radical ($PO_4$) to thereby produce and accumulate ATP in the medium.

The term "chemical substances showing the same metabolic route as methanol" as referred to herein means the substances which can be utilized with the same metabolic route as methanol, such as methylamine, formaldehyde, formic acid and methane.

Listed below are the examples of the ATP-producing bacteria having methanol assimilability that can be used in this invention: *Methylomonas probus* FERM-P 3193 (corresponding to ATCC 20563) and *Methylomonas methylovora* ATCC 21369 which belong to the genus Methylomonas; *Pseudomonas insueta* ATCC 21276, *Pseudomonas methanolica* ATCC 21704 and *Pseudomonas methanica* ATCC 21439 which belong to the genus Pseudomonas; *Protaminobacter ruber* ATCC 8457 and *Protaminobacter candidas* ATCC 21372 belonging to the genus Protaminobacter; *Achromobacter methanolophila* ATCC 21275 belonging to the genus Achromobacter; *Corynebacterium s.p.* ATCC 21232 belonging to the genus Corynebacterium; and *Bacillus cereus* ATCC 14579 belonging to the genus Bacillus.

As the techniques for producing the useful substances by utilizing the above-mentioned types of bacteria, the following reports are available: Growth of Microbes As Protein Source by Cultivation with Methanol-Based Media (Japanese Patent Laying-Open No. 28988/1977), Production of Flavin Adenine Dinucleotide (J. Ferment. Technol. 55, 630 (1977)), Production of Vitamin $B_{12}$ (Appl. Microbiol. 30, 477 (1975)), Production of Lipid and Polysaccharide. (Proceedings of the Conference of Japan Agricultural Chemical Society, 1978, Symposium Cl, Utilization of Microorganisms, 551–556), and Production of Amino-Acids (above-said Proceedings), but no report has ever been made on utilization of said types of bacteria for the purpose of production of ATP.

In the present invention said type of bacterium is cultivated in a medium containing methanol or a chemical substance showing the same metabolic route as methanol and an inorganic phosphate in an amount of 4–35 g/l as calculated in terms of $PO_4$. Methanol or said chemical substance is used as carbon source in the medium, but it should be noted that too high concentration of such substance in the medium adversely affects the growth of the bacterium. As for the concentration of such substance in the medium, it is usually recommended to be within the range of 0.2–4% by volume in the case of methanol and methylamine and in the range of 0.01–0.1% by volume in the case of formic acid and formaldehyde. In the case of methane, it is used in a concentration corresponding to its solubility.

Such carbon source may be added all at one time to the medium at the start of cultivation, but a better result is obtained in the yield of ATP by initially keeping low the carbon source concentration in the medium and supplementarily supplying the carbon source as that in the medium is consumed with advancement of cultivation.

In this invention, it is essential to have an inorganic phosphate contained in the medium in a concentration of 4–35 g/l as calculated in terms of $PO_4$ in addition to said carbon source. Such inorganic phosphate concentration in the medium corresponds to several ten times that in the ordinary bacterium culture media and is quite specific.

If the inorganic phosphate concentration (as measured in terms of $PO_4$) in the medium is below 4 g/l, there is provided no increase in the production of ATP, while if said concentration is higher than 35 g/l, the growth of the ATP-producing bacterium is retarded to reduce the yield of ATP. It is to be noted that an inorganic phosphate of high concentration functions to prevent the produced ATP from being secreted out of the bacterial body and decomposed by phosphatase.

The inorganic phosphates usable in this invention are of the type commonly employed for the fermentation media, and they include, for example, $(NH_4)_2HPO_4$, $KH_2PO_4$ and $K_2HPO_4$. The medium composition used in this invention may contain, in addition to said carbon source and inorganic phosphate, an inorganic salt such as of potassium, magnesium, iron, manganese, etc., and, in some cases, an inorganic salt of a metal such as zinc, cobalt, molybdenum, etc., as well as a nitrogen source such as ammonia, ammonium salt, urea, nitrate, etc. It is also possible to add a surfactant, defoamer and other additives.

The following is an exemplification of the medium composition used in this invention.
Carbon source 0.05–2% by vol.
$(NH_4)_2HPO_4$ 5–45 g/l (3.5–32 g/l in terms of $PO_4$)
$KH_2PO_4$ 0.5–2.5 g/l (0.35–1.75 g/l in terms of $PO_4$)
$K_2HPO_4$ 0.5–2.5 g/l (0.275–1.37 g/l in terms of $PO_4$)
$(NH_4)_2SO_4$ 0–1.0 g/l
$MgSO_4.7H_2O$ 0.5–5.0 g/l
$FeSO_4.7H_2O$ 0.05–0.5 g/l
$CaCl_2.2H_2O$ 0–0.2 g/l
$MnSO_4.4H_2O$ 0–0.2 g/l The cultivation of said ATP producing bacterium in said medium is preferably carried out under the following conditions: pH=5.8–9.0, preferable 6.0–8.0, temperature=15°–50° C., preferable 30°–40° C., and aeration rate=0.5–4.0 V.V.M. (volume of air (l)/volume of culture solution (l/min.)), under stirring at 40–600 r.p.m. for a period of 2–9 days. For adjusting pH of the culture medium, there may be used an alkaline material such as ammonia, an acidic material such as sulfuric acid, a buffering agent such as phosphate buffer, or other suitable substances such as urea, calcium carbonate, etc. In case of using an alkaline material, ammonia is most preferred as it can serve as a nitrogen source.

As said bacteria are fermented under the said cultivation conditions according to this invention, ATP is accumulated in the medium in high concentration of 2–12 g/l. After completion of fermentation, the microbes are removed and the produced ATP is separated and recovered by a known way. For instance, after removing the bacterial substance from the fermentation medium (broth), the supernatant solution is subjected to a combination of fractionation and concentration-precipitation by dint of adsorption and elution by using activated carbon and an anion exchange resin and the resultantly produced ATP is recovered.

According to this invention, as seen in the Examples which follow, ATP is produced and accumulated in the culture medium in a high concentration of over 2 g/l without adding adenine or its derivatives in the medium.

Shown in the following are some Examples of this invention to more definitely explaining the effects of this invention.

The amount of ATP produced in the medium in each Example was measured in the manner shown below by utilizing the principle of reaction between ATP and luciferin-luciferase expressed as follows:

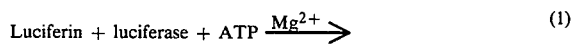
$$\text{Luciferin + luciferase + ATP} \xrightarrow{Mg^{2+}} \quad (1)$$
$$\text{adenyl-luciferin + pyrophosphate}$$

$$\text{Adenyl-luciferin} \xrightarrow{O_2} \text{adenyl-oxyluciferin} \quad (2)$$

The intensity of light in the wavelength region of 560–580 nm of fluorescence produced in the reaction of (2) above was measured for a given period of time by using CHEM-GLOW PHOTOMETER J4-7441 (American Instrument Co.) and its integral product was compared with the previously prepared known ATP standard solution calibration curve to thereby determine the amount of ATP produced in the culture solution.

EXAMPLE 1

A base medium was prepared by dissolving 7.0 g of $(NH_4)_2HPO_4$, 1.0 g of $KH_2PO_4$, 1.0 g of $K_2HPO_4$, 1.0 g of $MgSO_4.7H_2O$ and 0.1 g of $FeSO_4.7H_2O$ in 1 liter of ion exchange water, and 100 ml of this base medium was pipetted into each of the 300 ml Erlenmeyer flasks, and after sterilization, 1.6 g of methanol was further added into each said flask. Each of the thus prepared media was inoculated with *Methylomonas probus* FERM-P 3193 which had been previously cultivated with an agar slant medium of said composition and subjected to shaking culture at 30° C. At the 4th day after start of culture, 2.8 g/l of ATP was produced and accumulated in the culture solution.

1 liter of this culture solution was subjected to a heat treatment at 80° C. for 5 minutes, and after cooling, it was centrifuged to get rid of the bacterial body, and the supernatant solution, adjusted to pH 3.5 with 3N hydrochloric acid, was further subjected to an active carbon treatment to have ATP adsorbed on active carbon and then ATP adsorbed on active carbon was eluted with a 50% alcohol solution containing 1.4% of ammonia. This eluate was concentrated under reduced pressure and at a low temperature to eliminate excess ammonia, adjusting pH to around 8.0.

Then the concentrated solution was passed through a column of strongly basic anion exchange resin Dowex (trademark) 1-X2 (Cl⁻) which had been previously adjusted to Cl type, thereby having ATP adsorbed on the column. The adsorbate was washed with ion exchange water and eluted with a mixed solution of hydrochloric acid and sodium chloride (a 0.2M NaCl solution formed by dissolving a 0.02M HCl solution (pH 1.7) in NaCl) and the ATP fraction was separated.

This eluate was neutralized with sodium hydroxide, passed through a column packed with active carbon and eluted with 15% ammonia water and the resultant eluate was concentrated under heating to drive out ammonia. By adding methanol to said concentrated solution, there was obtained 2.2 g of crystals of sodium salt of ATP.

EXAMPLE 2

20 liters of a medium prepared by dissolving 7.0 g of $(NH_4)_2HPO_4$, 1.0 g of $KH_2PO_4$, 1.0 g of $K_2HPO_4$, 2 g of $MgSO_4.7H_2O$ and 0.2 g of $FeSO_4.7H_2O$ and 0.2 ml of a defoaming agent KS-66 in 1 liter of ion exchange water was charged into a 30-liter jar fermentor and sterilized at 120° C. under pressure of 1.2 kg/cm$^2$ for 30 minutes. After cooling, said medium was added with 200 ml of methanol and inoculated with 2% of seed culture (*Methylomonas probus* FERM-P 3193) which had been cultivated with the same medium as said above, followed by aeration at a rate of 20 1/20 1 (liquid quantity)/min (0.5 V.V.M.) under stirring at 500 r.p.m. at 35° C. The aeration rate was elevated to 20 1/20 1/min (1.0 V.V.M.) with growth of the bacterium, and cultivation was performed for the total period of 96 hours. The pH of the medium was automatically controlled to 6.0–7.2 with ammonia water during cultivation while methanol consumption was measured by gas chromatography, with methanol being automatically suppllied so that its concentration would always stay within the range of 0.3–2.0%. In 96 hours after start of cultivation, 5.3 g/l of ATP was produced and accumulated in the culture solution. ATP in the culture solution was recovered in the same way as desdribed in EXAMPLE 1.

EXAMPLE 3

Cultivation was carried out under the same conditions as described in EXAMPLE 2 except that the amount of $(NH_4)_2HPO_4$ in the medium was increased to 20 g/l. 12 g/l of ATP was produced and accumulated in the culture solution in 96 hours after start of the cultivation. ATP was recovered according to the same procedure as described in EXAMPLE 1.

EXAMPLE 4

The cultivation process of EXAMPLE 2 was repeated except for by using 30 g/l of $(NH_4)_2HPO_4$ in the medium. 7 g/l of ATP was produced and accumulated in 96 hours after start of the cultivation. ATP was recovered after the same manner as described in EXAMPLE 1.

COMPARATIVE EXAMPLE 1

Cultivation was carried out under the same conditions as described in EXAMPLE 2 except that the amount of $(NH_4)_2HPO_4$ in the medium was reduced to 3 g/l. Only 0.2 g/l of ATP was produced in the culture solution in 96 hours after start of the cultivation.

COMPARATIVE EXAMPLE 2

Cultivation was carried out under the same conditions as described in EXAMPLE 2 except that the amount of $(NH_4)_2HPO_4$ was increased to 50 g/l. There was produced only 1.0 g/l of ATP in the culture solution in 96 hours after start of the cultivation.

EXAMPLE 5

Cultivation was carried out under the same conditions as described in EXAMPLE 3 by using the strains shown in the following table. The resultant ATP yields are as shown in the following table.

TABLE

| Strain | | ATP yield g/l |
| --- | --- | --- |
| *Methylomonas methylovora* | ATCC 21369 | 3.5 |
| *Pseudomonas insueta* | ATCC 21276 | 3.1 |
| *Pseudomonas methanolica* | ATCC 21704 | 3.6 |
| *Pseudomonas methanica* | ATCC 21439 | 3.2 |
| *Protaminobacter ruber* | ATCC 8457 | 2.7 |
| *Protaminobacter candidus* | ATCC 21372 | 2.5 |
| *Corynebacterium s.p.* | ATCC 21232 | 2.3 |
| *Bacillus cereus* | ATCC 14579 | 2.2 |
| *Achromobacter methanolophila* | ATCC 21275 | 2.4 |

What is claimed is:

1. A process for making adenosine-5'-triphosphate comprising the steps of cultivating an adenosine-5'-triphosphate-producing bacterium selected from the group consisting of *Methylomonas methylovora, Pseudomonas insueta, Pseudomonas methanolica, Pseudomonas methanica, Protoaminobacter ruber, Protoaminobacter candidas, Achromobacter methanolophila* and *Bacillus cereus* in a culture medium free of added adenine and of any compound containing an adenine moiety containing as a substrate a substance selected from the group consisting of methanol, methane, methylamine, formaldehyde and formic acid, and an inorganic phosphate in an amount so that the concentration of phosphate ($PO_4$) is 4 to 35 g/liter, said substance being contained in said culture medium from the beginning of an throughout the cultivating step, thereby causing said bacterium to produce adenosine-5'-triphosphate, separating the proliferated bacteria from the culture medium and isolating the adenosine-5'triphosphate produced from the culture medium.

2. A process according to claim 1, wherein the culture medium contains methanol as a substrate.

3. A process according to claim 2, wherein the culture medium contains 0.2 to 4% by volume of methanol.

4. A process according to claim 1, wherein the inorganic phosphate is selected from the group consisting of diammonium hydrogen phosphate, potassium dihydrogen phosphate and dipotassium hydrogen phosphate.

5. A process according to claim 1, wherein the cultivation of the bacterium is carried out in the culture medium at a pH of 6.0 to 8.0 and a temperature of 30° to 40° C. while blowing air into the culture medium at an aeration rate of 0.5 to 4.0 volume/unit volume of the culture medium per minute.

6. A process for making adenosine-5'-triphosphate comprising the steps of cultivating *Methylomonas probus*, in a culture medium free of added adenine or its derivative and containing as a substrate a substance selected from the group consisting of methanol, methane, methylamine, formaldehyde and formic acid, and an inorganic phosphate in an amount so that the concentration of phosphate ($PO_4$) is 4 to 35 g/liter, said bacteria from the culture medium and isolating the adenosine-5'-triphosphate produced from the culture medium.

7. A process according to claim 6, wherein the culture medium contains methanol as a substrate.

8. A process according to claim 6, wherein the culture medium contains 0.2 to 4% by volume of methanol.

9. A process according to claim 6, wherein the inorganic phosphate is selected from the group consisting of diammonium hydrogen phosphate, potassium dihydrogen phosphate and dipotassium hydrogen phosphate.

10. A process according to claim 6, wherein the cultivation of the bacterium is carried out in the culture medium at a pH of 6.0 to 8.0 and a temperature of 30° to 40° C. while blowing air into the culture medium at an aeration rate of 0.5 to 4.0 volume/unit volume of the culture medium per minute.

* * * * *